(12) United States Patent
Chandler et al.

(10) Patent No.: US 7,780,914 B2
(45) Date of Patent: Aug. 24, 2010

(54) SAMPLE COLLECTION AND TESTING SYSTEM

(75) Inventors: Howard Milne Chandler, Yarmouth, ME (US); Lawrence Charles La Pointe, New South Wales (AU)

(73) Assignee: Enterix Pty, Limited

( * ) Notice: Subject to any disclaimer, the term of this patent is extended or adjusted under 35 U.S.C. 154(b) by 906 days.

(21) Appl. No.: 11/086,885

(22) Filed: Mar. 22, 2005

(65) Prior Publication Data

US 2005/0181517 A1    Aug. 18, 2005

Related U.S. Application Data

(63) Continuation of application No. 09/936,452, filed as application No. PCT/AU00/00180 on Mar. 10, 2000, now abandoned.

(30) Foreign Application Priority Data

Mar. 11, 1999    (AU) .................... PP9157

(51) Int. Cl.
   *G01N 21/00* (2006.01)
   *G01N 21/77* (2006.01)

(52) U.S. Cl. ............... 422/58; 422/60; 436/169

(58) Field of Classification Search ........... 422/58, 422/60; 436/169
See application file for complete search history.

(56) References Cited

U.S. PATENT DOCUMENTS

| | | | |
|---|---|---|---|
| 5,169,789 A | 12/1992 | Bernstein | 436/501 |
| 5,677,133 A * | 10/1997 | Oberhardt | 435/7.1 |
| 5,795,543 A | 8/1998 | Poto et al. | 422/82.05 |
| 5,824,268 A | 10/1998 | Bernstein et al. | 422/56 |
| 5,869,003 A | 2/1999 | Nason | |
| 5,939,252 A | 8/1999 | Lennon et al. | 435/4 |
| 6,009,632 A | 1/2000 | Douglas | 33/562 |
| 6,027,943 A | 2/2000 | Kang et al. | 436/518 |
| 6,165,416 A | 12/2000 | Chandler | 422/58 |
| 6,241,689 B1 | 6/2001 | Chard et al. | 600/584 |
| 6,555,390 B2 | 4/2003 | Chandler | 436/518 |
| 6,565,808 B2 | 5/2003 | Hudak et al. | 422/58 |
| 6,727,073 B1 | 4/2004 | Moore et al. | 435/7.32 |

FOREIGN PATENT DOCUMENTS

| | | |
|---|---|---|
| AU | 47895/90 | 1/1990 |
| DE | 198 22 770 A1 | 11/1999 |
| JP | 03-128461-0 | 5/1991 |

(Continued)

OTHER PUBLICATIONS

Office Action for Japan Patent Application No. 2000-604203.

*Primary Examiner*—Lore Jarrett
(74) *Attorney, Agent, or Firm*—Foley & Lardner LLP

(57) ABSTRACT

A testing device for the identification of an analyte of interest in a sample, comprises a housing having an internal recess (14); a sample collection device (19) and at least one insertable testing element (20); the housing being adapted to receive the sample collection device in the internal recess therein and to shield a sample collected on the sample collection device, the housing also being adapted to receive the or each insertable testing element such that, on insertion of the testing element into the housing, the testing element is in liquid conductive communication with a sample collected on the sample collection device.

24 Claims, 3 Drawing Sheets

FOREIGN PATENT DOCUMENTS

| | | |
|---|---|---|
| JP | 05-503230-0 | 6/1992 |
| JP | 09-318623-0 | 12/1997 |
| WO | WO 92/10136 | 6/1992 |
| WO | WO 96/40434 | 12/1996 |
| WO | WO 98/00712 | 1/1998 |
| WO | WO 99/04267 | 1/1999 |

* cited by examiner

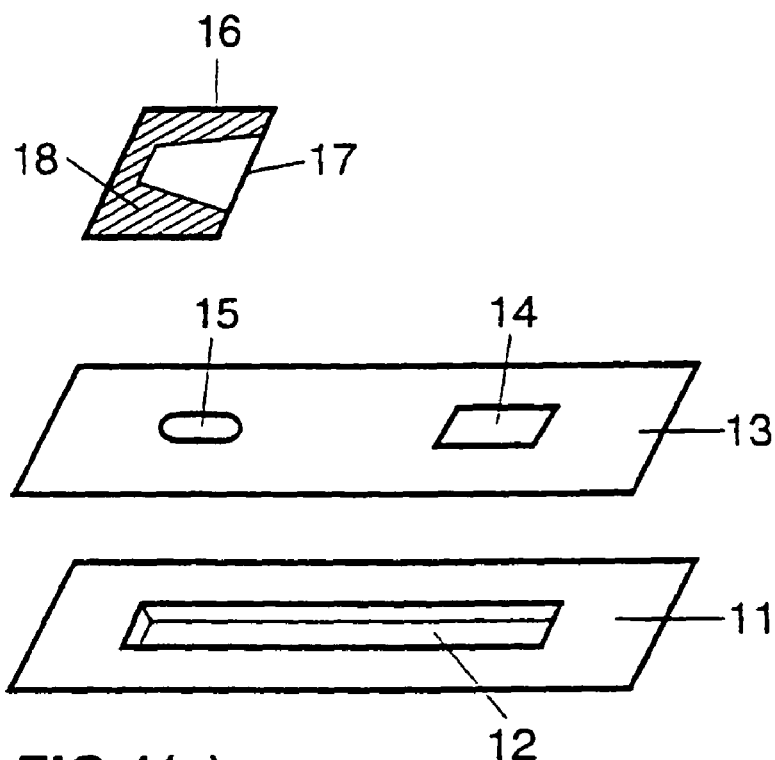
FIG 1(a)
FIG 1(b)
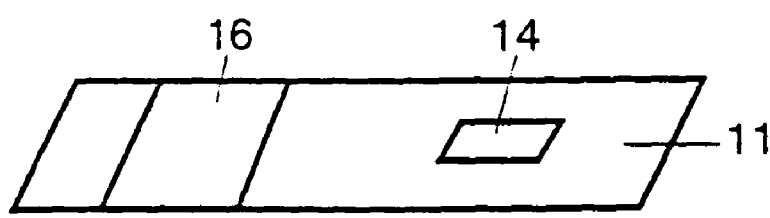
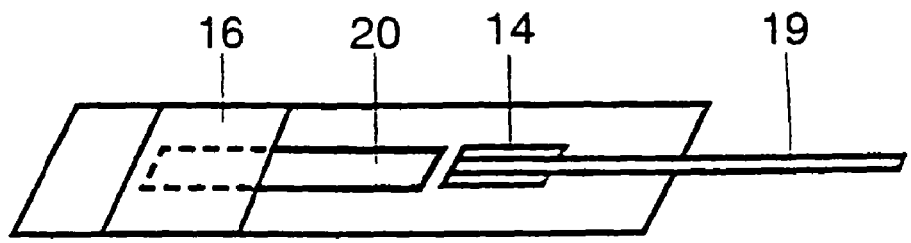
FIG 1(c)

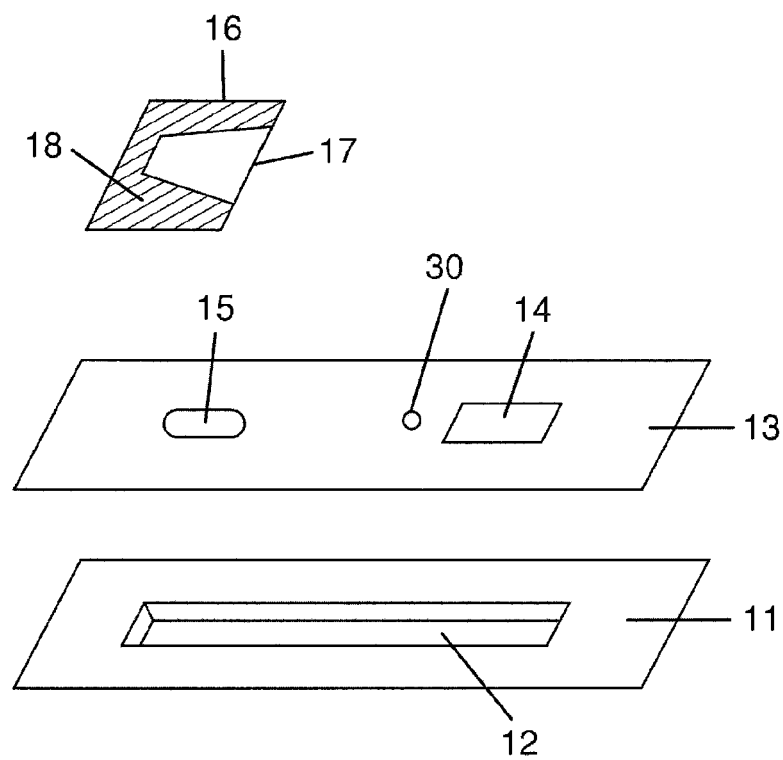
FIG 4(a)
FIG 4(b)
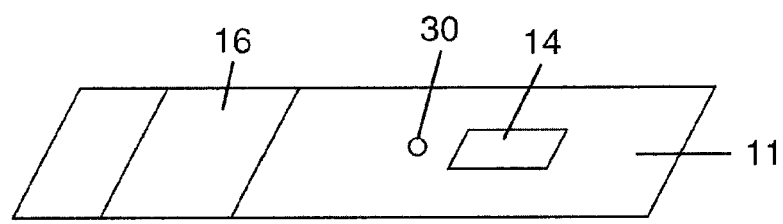
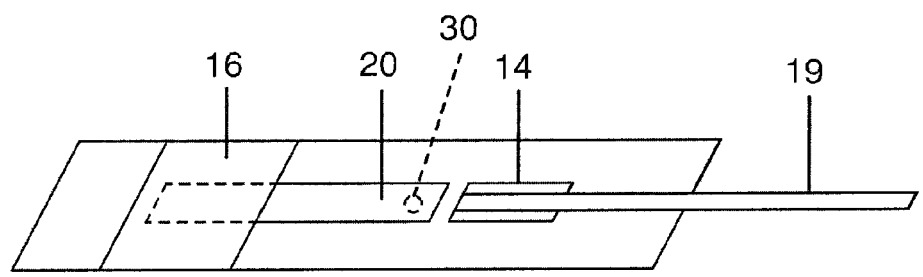
FIG 4(c)

SAMPLE COLLECTION AND TESTING SYSTEM

CROSS REFERENCE TO RELATED APPLICATIONS

The present application is a continuation (and claims the benefit of priority under 35 USC 120) of U.S. application Ser. No. 09/936,452, filed Dec. 28, 2001, now abandoned which is a U.S. National Phase application of PCT/AU00/00180, filed Mar. 10, 2000, which claims priority from Australian application no. PP 9157, filed Mar. 11, 1999. The disclosure of the prior applications are considered part of (and are incorporated by reference in) the disclosure of this application.

FIELD OF THE INVENTION

This invention relates to an apparatus and method for the collection and testing of a sample to detect an analyte in the sample, particularly but not exclusively by immunodiagnostic testing. The format of the collection and testing system of the present invention is particularly useful for ascertaining the health status of a human or other animal or a plant or other life form, or the environmental status of a geographical or industrial location by ascertaining the presence or absence of an analyte in a sample. Although useful for immediate sample application and test development, the format is particularly applicable in those circumstances where the sample is collected at one site for test development at another location.

BACKGROUND OF THE INVENTION

A variety of diagnostic devices have been developed for the detection of an analyte of interest in a sample. In those devices in which sample collection and testing functions are non-linked, the transfer of collected sample to testing apparatus introduces a potential source of error. In those devices in which sample collection and testing functions are linked, the devices are dedicated in their entirety to the detection of a particular analyte and are not easily adaptable to a wide range of analyte detection.

With respect to mammalian systems (e.g. humans), samples amenable to analysis using the testing device of the present invention include biological fluids (e.g. blood, urine, semen, saliva, etc.) or excrements. Such biological fluids can carry a variety of analytes, the presence of which can be diagnostic for a particular disease state. The application of the subject invention to the detection of disease states in humans is of primary importance. However, in addition to use in the context of the diagnosis of serious disease states, the present invention is also useful in a variety of other contexts. Applications in connection with the analysis of microbes, plants, animals, food and water are all anticipated.

For example, ground water samples can be analysed for the presence of contaminants such as atrazine. Food, such as ground beef, can be analysed for the presence of contamination by bacteria such as *E. coli*. In the plant kingdom, the present invention can be applied to the analysis of, for example, pollen, spores and plant vascular fluids. Generally speaking, the only requirement for detection using the device and method of the present invention is that the analyte of interest should be soluble or suspendible in an aqueous solution.

The present invention relates to a device which is useful inter alia for the detection of any aqueous soluble or suspendible analyte which is detectable, for example, on the basis of immunological and/or chemical properties. An example of an analyte detected by its immunological properties includes, but is not limited to, an immune interacting molecule such as an antigen, hapten, immunoglobulin or T-cell derived antigen binding molecule. An example of an analyte detected by chemical properties includes an enzyme, catalyst or ligand. Thus, in detection of occult gastrointestinal bleeding as a screen for colo-rectal cancer, using the faecal occult blood (FOB) test, the device of the present invention can be adapted to either guaiac-based testing, or immunological testing. The preferred format for immunological testing is immunochromatography. This format is described generally in U.S. Pat. Nos. 5,591,645 and 5,622,871, the disclosures of which are incorporated herein by reference.

Prior to discussing the invention in greater detail, a brief review of the immunochromatography process will be provided to establish certain principles. To detect an analyte of interest by immunochromatography, two binding reagents which bind specifically and non-competitively to the analyte of interest may be employed. A first specific binding reagent is labelled and is free to migrate. When introduced to a sample to be tested for the presence of the analyte of interest, the first specific binding reagent binds to the analyte of interest, if present. The second specific binding reagent is immobilized in a detection zone on a liquid-conductive solid phase material, the detection zone being remote and downstream from the location of initial contact between the first binding reagent and the analyte of interest. A solvent front carrying the mobile first specific binding reagent complexed with analyte of interest (if present) migrates along the liquid-conductive solid phase material through the detection zone. If analyte is present in the sample, the immobilised second specific binding reagent binds the analyte thereby forming an immobilised sandwich complex comprising the first specific binding reagent (which is labelled), the analyte of interest, and the second specific binding reagent (which is immobilised). Detection of the label immobilised in the detection zone is indicative of the presence of analyte of interest in the sample. In most embodiments, the first and second specific binding reagents are either polyclonal or monoclonal antibodies.

Many diagnostic tests and assays involve the use of samples collected in the field and then either tested immediately, or returned to a central facility for later test development. Such samples may include blood, serum, saliva, milk, faeces, urine or other materials of biological origin, or samples collected from the environment, such as water for analysis for nutrients or contamination.

For example, in the practice of medicine, one or more blood samples may be drawn from a patient in the physician's office and then sent to a pathology laboratory for subsequent testing for one or more analytes. Typically the blood is drawn by venipuncture, using an especially designed needle and blood collection tube (e.g. Vacutainer, Becton Dickinson). The collection of the blood by venipuncture requires trained personnel, the provision of suitable facilities and equipment, refrigerated transport and storage facilities, and finally means for accurate sampling, treatment (e.g. serum or plasma separation) and dispensing of the blood/plasma/serum into the test or assay equipment. In many cases the blood is only used for one test and, if an effective collection means were available, the blood from a finger prick would be sufficient.

Recently, there has been a marked increase in the use of "Point of Care" (POC) testing, using rapid, self-developing test systems packaged in simple, single-use, disposable test devices. Such POC tests include assays for glucose monitoring, pregnancy and infections such as Streptococcal infection of the throat and *Chlamydia* infection of the genital tract. Many of these tests, however, introduce a limitation that the test must be conducted immediately at the test site, as the tests have been designed such that the addition of the sample initiates the test. In addition, these tests generally do not incorporate a sample collection system, but rely on the sample being obtained at the time of testing, or else being presented in a separate collection vessel, such as a Vacutainer, as described above.

For many test systems, it is desirable for the sample to be tested to be collected at one site for subsequent test development at another site. In such instances, it is desirable to have a simple, inexpensive and safe means of delivering this testing option, preferably by means of an integral collection and testing system.

Ideally, the prerequisites for such an integrated collection and test system would include:

generic design, that is, one basic format to suit all test applications;

simple, accurate and representative sampling, requiring minimal skills and equipment to collect the sample;

safe, stable, and inexpensive storage of the sample;

effective reconstitution and/or displacement of the sample to the testing means for development of the test; and cost-effective delivery of the test result.

It is an object of the present invention to provide a test format that meets these requirements and is suited for the delivery of samples for either immediate or later testing.

SUMMARY OF THE INVENTION

In one aspect, the present invention provides a device for use in the collection and testing of a sample, comprising:
a. a housing having an internal recess; and
b. a sample collection device;

said housing being adapted to receive said sample collection device in the internal recess therein and to shield a sample collected on said sample collection device, said housing also being adapted to receive an insertable testing element, such that on insertion of said testing element into said housing, the testing element is in liquid-conductive communication with a sample collected, on said sample collection device.

In another aspect, the present invention provides a testing device for the identification of an analyte of interest in a sample, comprising:
a. a housing having an internal recess;
b. a sample collection device; and
c. at least one insertable testing element;

said housing being adapted to receive said sample collection device in the internal recess therein and to shield a sample collected on said sample collection device, said housing also being adapted to receive the or each said insertable testing element such that, on insertion of said testing element into said housing, the testing element is in liquid-conductive communication with a sample collected on said sample collection device.

In another aspect, the present invention provides a method for the identification of an analyte of interest in a sample by use of a testing device as broadly described above, comprising:
a. collecting a sample on the sample collection device,
b. inserting said sample collection device into the internal recess of the housing of the testing device,
c. inserting the insertable testing element into the housing such that the testing element is in liquid-conductive communication with said sample, and optionally
d. applying a solvent to said sample to enable transfer of at least part of said sample, or a component thereof, to the testing element.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

An important feature of the testing device of the present invention is that the single device serves a collection and testing function. However, the testing function is not linked to collection of a sample. That is, the collection of a sample (e.g. by a patient in the home) and application to the testing device does not yield a test result. In order to determine the test result, an insertable testing element must be inserted into the device, and if the sample has previously been dried or desiccated the sample must be rehydrated.

Preferably, the sample is a liquid containing sample. The sample may itself be a liquid or it may be in a particulate or solid form which is then hydrated prior to testing. In a preferred but not essential aspect of this invention, the testing device is adapted so that a sample applied to the sample collection device (for example, by a patient in the home) may be dried or desiccated on the sample collection device within the housing of the testing device.

In accordance with this invention, the testing element is adapted to be inserted into the housing of the device so that the testing element is in liquid-conductive communication with the sample collection device as described above.

Preferably, the housing is provided with a first window or aperture communicating with the internal recess within the housing for insertion of the sample collection device, together with at least one additional window or aperture which is separate from the first window or aperture and which also communicates with the internal recess for insertion of the, or each, insertable testing element so that the testing element is in liquid-conductive communication with a sample collected on said sample collection device.

As used herein, the term "liquid-conductive communication" shall be taken to mean that a solvent applied to a sample is capable of being in liquid-conductive communication with the testing element under sufficient conditions of hydration to enable transfer of at least part of said sample, or a component thereof, to the testing element.

The three components of a preferred embodiment of the testing device of the present invention are:
1. a sample collection device designed to collect, and store, a predetermined (that is a quantified or semi-quantified) amount of sample,
2. a housing having an internal recess designed to accept and protect the sample collection device and, if required, offer sufficient ventilation to allow dehydration of a liquid sample collected on the sample collection device, and
3. a testing element designed so that, on insertion into the housing, liquid-conductive contact is established with the sample collection device.

Each of the components is designed, or selected, for its suitability for inexpensive, high-speed, automated manufacture by established manufacturing technologies.

The sample collection device is designed to enable sample collection without the requirement for laboratory facilities, equipment, or highly trained or skilled personnel. For some applications, the collection device may be an existing device, such as a swab. Other applications will require a custom designed device to accurately meter, accept and store a predetermined amount of specimen. In many cases, this component will consist of a hydrophilic, porous matrix, of defined volumetric capacity, affixed to the base of a dipstick or handle, so that collection of a sample involves touching the matrix to the sample, thus filling the matrix with a measured volume of the sample. The preferred embodiment of the sample collection device described herein is designed for manufacture by established high-speed laminating and die-cutting processes.

The housing is also designed for manufacture by rapid packaging technologies, such as "Form, Fill and Seal" technology. The housing has an internal recess which serves to store and protect the sample, as well as facilitate the transfer of the sample to the testing element at the time of test initiation. It may also house or receive any reagents necessary for initiation or completion of the test procedure.

In many instances, the testing element will be an immunochromatographic test strip, such as are used in numerous existing POC tests. Most of the existing tests, however, have the test strip mounted in a housing so that the addition of the sample initiates the development of the test. These tests are therefore not suitable for remote sampling and centralised test development. In addition, the existing POC tests are expensive to manufacture. The test strip and housing components must be assembled and then stored dry, as the reagents in the test strip are subject to rapid degradation in the presence of humidity. Desiccated packaging of significant cost and volume must therefore be provided. In accordance with the present invention, the test strip is inserted into the housing at the time of testing, thus avoiding any assembly costs. These test strips may also be stored in bulk, for example in a desiccated container, thus saving on packaging and storage costs.

In another embodiment of the present invention, the testing device may comprise two or more insertable testing elements each of which, when inserted, is in liquid-conductive communication with the sample collection device. In this embodiment, the testing elements may be either the same or they may be different. In the former case, replicate tests may be carried out on the sample applied to the sample collection device. In the latter case, different tests may be carried out on the same sample applied to the sample application matrix. By way of example, in FOB testing for screening for colo-rectal cancer, one insertable testing element may be a guaiac-based test strip, whilst another insertable testing element may be an immunochromatographic test strip.

Given the description which follows, one of skill in the art will recognize that the testing element or elements may be provided in an array of alternative embodiments. Referring to the immunochromatographic embodiment, for example, a required element of the test strip is a liquid-conductive solid phase material to which a detection reagent (described above in the brief review of immunochromatography as the second specific binding reagent) may be immobilized. This solid phase material is preferably nitrocellulose. Nitrocellulose is a charged matrix to which an appropriately charged reagent, such as a monoclonal antibody, may be immobilized without prior chemical treatment. Alternatives such as filter paper may also be used, however, chemical coupling (e.g., CNBr coupling) is required to attach a charged reagent such as an antibody to a matrix of this type.

A preferred liquid-conductive solid phase material is a nitrocellulose membrane having a pore size of at least about 1 micron. Nitrocellulose membranes best adapted for use in connection for immunochromatography of this type have a pore size of about 5-20 microns. The selection of particular pore size dictates flow rate. Depending upon the particular application, a faster or slower flow rate may be indicated and an appropriate solid phase material is selected.

To facilitate handling, it is desirable to provide a backing to the nitrocellulose membrane. A thin plastic sheet stock (e.g., lexan or polystyrene) may be cut to provide a suitable water resistant backing for the solid support. Such sheet stock is selected so as not to interfere with the reading of a test result. For example, the selection of a white or clear sheet stock is generally preferred. In an alternative embodiment, the liquid conductive solid phase material may be sandwiched between such water resistant sheet stock.

When inserted into the housing, the or each testing element is designed to be in liquid-conductive communication with the sample collection device. Preferably, this liquid-conductive communication is direct, for example between the sample collection device and the liquid-conductive solid phase material of an immunochromatographic or other testing element. In a preferred immunochromatography embodiment, additional liquid-conductive elements may be incorporated in or on the testing element. For example, a conjugate pad may be provided which, in use, is disposed between the sample collection device and the liquid-conductive solid phase material of the testing element. As will be discussed in greater detail below, the conjugate pad provides a matrix for the deposition of a labelled detection reagent which is free to migrate when rehydrated (the first specific binding reagent in the brief review of immunochromatography provided above). The sample may be dehydrated or desiccated within the sample collection device prior to the insertion of the testing element. At the time of rehydration during the testing step, the labelled detection reagent within the conjugate pad is also resuspended and resolubilised. If analyte is present in the sample, the labelled reagent binds to the analyte and the complex is carried along with the solvent front to the detection zone of the testing element.

At the end of the testing element distal to the conjugate pad when in use, an optional absorbent pad is attached, in communication with the liquid-conductive solid phase material. This pad provides a solvent sink which drives the migration of the liquid sample through the detection zone. It is important that the absorbent pad have sufficient volume to drive the migration to the extent that substantially all unbound labelled detection reagent is carried beyond the detection zone of the testing element. One of skill in the art will recognize that an absorbent pad is a non-essential element. The need for this element can be obviated, for example, by extending the length of the liquid-conductive solid phase material beyond the detection zone such that a sufficient volume is carried through the detection zone.

In use, a sample is collected on the sample collection device in a conventional manner. For example, in FOB testing, a faecal smear may be collected on the sample collection device, or alternatively, toilet bowl water May be sampled using an absorbent swab. In the latter sampling method, a short time may be allowed for haemoglobin to diffuse from the stool prior to sampling, or the swab may be used as the sample collection device to disperse the stool into the toilet bowl water. The swab is then used to sample the water.

Depending upon the nature of the analyte, the testing device with sample collection device inserted into the internal recess of the housing of the device may be stored in this form for a period of days, weeks or months prior to testing. To determine the presence of an analyte, the sample is rehydrated by adding an appropriate solvent to the sample collection device. The solvent may be added through a solvent application aperture in the housing which is in communication with the sample collection device. Preferably, solvent applied through such a solvent application aperture should migrate through the region of the sample collection device where sample was actually applied, prior to reaching the point on the sample collection device which is in liquid-conductive communication with the testing element.

The labelled detection reagent may be introduced into the immunochromatography assay in a variety of ways. For example, the labelled detection reagent may be solubilized in the solvent used to rehydrate the contents of the sample collection device prior to the resolubilisation of the sample or its components. Alternatively, as discussed above, the labelled detection reagent may be introduced in solution into the conjugate pad and desiccated in situ. In this embodiment, the labelled detection reagent is resolubilized as the resolubilization solvent migrates from the sample collection device to the testing element. In yet another embodiment, a solution containing the labelled detection reagent may be added to the sample collection device prior to the application of the sample. This solution is then desiccated in situ. In this embodiment, analyte of interest, if present, and labelled detection reagent will be solubilized from the dry sample collection device at the time of testing.

Of the embodiments described in the preceding paragraph, the use of a conjugate pad is preferred for most embodiments. The addition of the labelled detection reagent to the resolubilization solvent prior to sample resolubilization has the disadvantage of using the expensive detection reagent (which could require storage at 4° C.) in an inefficient manner. With respect to the desiccation in situ of the labelled detection reagent in the sample collection device prior to sample collection, this would result in the establishment of a testing device in which the sample collection device is dedicated to a particular assay. One of the many benefits of the disclosed device is the fact that the housing (together with other elements of the device excluding the testing element) is totally generic. Thus, the housing of the testing device as well as the sample collection device can be purchased in bulk and stored as needed for any of a variety of testing requirements. The relatively expensive test-specific component is the testing element which can be selected for a particular need and used in conjunction with the generic housing and sample collection device.

Preferably the labelled detection reagent is a monoclonal or polyclonal antibody specific for a first epitope of the analyte of interest, coupled to a detectable label. The detectable label can be coupled to the antibody by any of the applicable techniques known in the art including, for example, covalent bonding and passive adsorption.

The detectable label may be a direct or an indirect label. A direct label is a label which is readily visible in its natural state, either to the naked eye, or with the aid of optical devices. A label which is visible only in the presence of external stimulation, such as ultraviolet light, is also considered to be a direct label. Examples of direct labels include dye sols (e.g., colloidal carbon), metallic sols (e.g., gold and iron), fluorescent particles and coloured latex particles.

Indirect labels require the addition of one or more developing reagents, such as substrates, to facilitate detection. Such labels include, for example, enzymes such as alkaline phosphatase and horseradish peroxidase.

The immobilized capture reagent is also typically a monoclonal or polyclonal antibody which is specific for a second epitope or range of epitopes on the analyte of interest. Thus, analyte present in the sample, whether bound by the detection reagent or not, is bound by the immobilized binding reagent in the detection zone. In a case in which a direct label is employed, a visible line appears on the liquid-conductive solid support as bound label accumulates in the detection zone. The appearance of this line may be diagnostic for the presence of analyte of interest in the sample.

An optional control zone can also be integrated into the testing element. The function of a control zone is to convey an unrelated signal to the user which indicates only that the testing process is complete and that the binding interaction which results in the detectable unrelated signal has taken place as expected. For example, the control zone may comprise an "anti-mouse" polyclonal antibody immobilized to the liquid-conductive solid phase material, preferably downstream of the detection zone. Assuming that the detection reagent is a murine monoclonal antibody linked to a detectable label, detection reagents not bound in the detection zone through a sandwich interaction involving the analyte of interest will ultimately bind in the control zone. In the absence of a signal in the detection zone, a control zone signal would indicate to the user that, for example, the sample contained nothing that resulted in general interference with an immunological assay. It can be imagined, for example, that extremes of pH or salt concentration could result in general interference through conformational changes or physical destruction on one or more of the participants in the immunologically based interaction to be detected. The inclusion of a control zone functions to provide a degree of confidence with respect to such variables.

The analyte of interest is determined in advance to be one which is diagnostic of a particular condition. For example, in connection with FOB tests, the analyte of interest is preferably human hemoglobin. Other examples of analytes of interest are described below.

The method and apparatus of the present invention is applicable to detecting analytes in humans and other animals. Other animals include primates, livestock animals (e.g. cows, sheep, horses, donkeys, pigs), laboratory test animals (e.g. rabbits, mice, rats, guinea pigs, hamster), companion animals (e.g. dogs, cats) and captive wild animals. The present invention also extends to detecting analytes in plants (e.g. monocotyledons and dicotyledons) and other life forms (e.g. microbes, yeasts, fungi, moulds). The present invention may also be used to detect analytes in geographic and industrial locations, including soil, oceans, rivers, water storage regions, toxic waste dumps, building sites, mining areas (e.g. coal, bauxite, uranium, graphite amongst many others) as well as in the air. The health status of humans, and other animals or plants or other life forms may be deduced or determined in the presence or level of analyte or by the absence of analyte. The environmental status may also be ascertained such as determining the presence of contaminants in various geographic or industrial locations.

BRIEF DESCRIPTION OF THE DRAWINGS

FIG. 1 illustrates a testing device in accordance with the present invention which is particularly adapted for use with samples or specimens collected on an absorbent swab.

FIG. 4 illustrates the testing device of FIG. 1 with the additional feature of a solvent application aperture 30.

DESCRIPTION OF PREFERRED EMBODIMENTS

Figure 2:
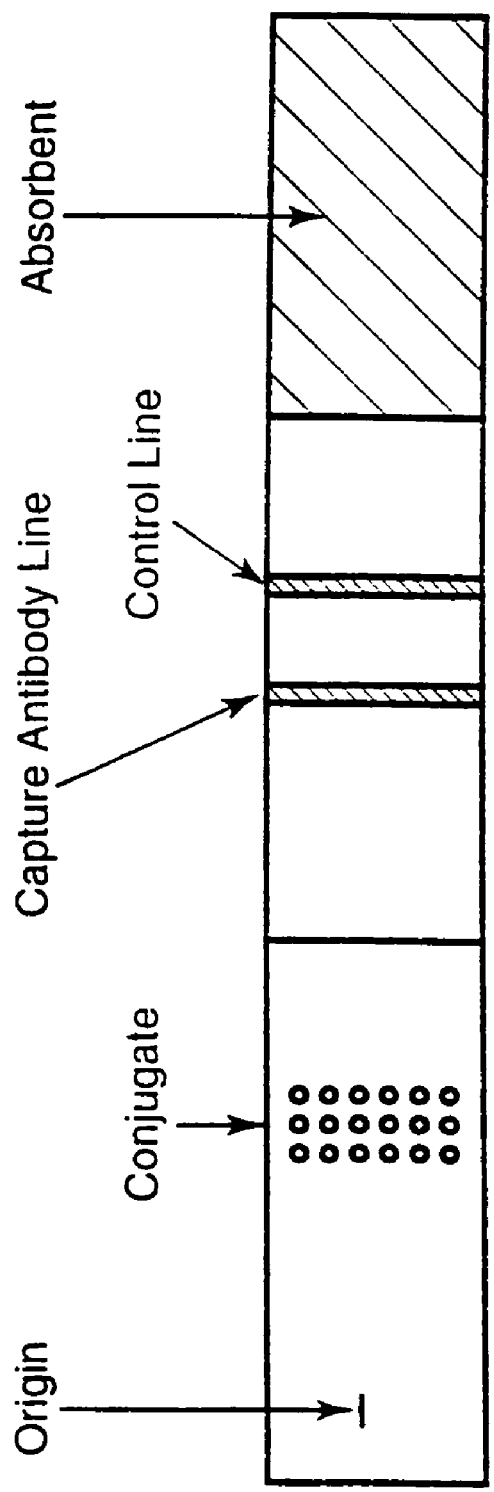
FIG. 2 illustrates an immunochromatographic test step for use in the testing device of the present invention.

FIG. 1 illustrates the testing device of the present invention in a format which uses a swab as the sample collection device. A swab may be used as a general sampling device for many liquid or moist specimen types, provided that they do not require an accurately measured volume of sample. Swabs are frequently used for obtaining infectious clinical samples, for example for testing for *Streptococcus pyogenes* Type A (Strep.A) in cases of throat infection.

The current POC tests for Strep.A use a swab to collect a sample or specimen from the region of the throat suspected of being infected. Reagents are added to the head of the swab to form nitrous acid, typically sodium nitrite solution and a weak acid such as acetic acid. Nitrous acid acts on the Strep.A bacteria to release its diagnostically specific antigen. This extraction of antigen may be "off board", for example in a reaction cup provided with the test, or "onboard", with the swab inserted into a receptacle in the housing of the test. Typically, an extraction time of 1 minute is allowed for release of antigen before commencement of the test.

FIG. 1(*a*) is an exploded drawing showing the general construction of the housing of the testing device of this embodiment of the invention, while FIG. 1(*b*) shows the assembled housing.

In this embodiment, the housing comprises a base (11) which is preferably made of a plastic that may be vacuum or pressure formed to provide a recess or cavity (12), as illustrated. A cover (13), preferably made of plastic or other waterproof material and provided with two openings (14) and (15) is sealed to the base (11), but not the recess (12), by adhesive or other sealing or aperture means. A plastic cover strip (16) is sealed to the cover (13), as illustrated so that the aperture (15) is covered, but with the strip remaining open along one edge (17). The shaded areas (18) on the cover strip (16) represent the sealing or glue pattern.

FIG. 1(*c*) shows the assembled housing with a swab (19) inserted in the recess (12) and immunodiagnostic test strip (20) inserted under the plastic cover strip (16).

FIG. 2 illustrates the generalised construction of an immunodiagnostic test strip suitable for use with this testing device.

When the swab (10) is fully inserted into the recess (12) in the housing via the aperture (14), its head (which contains the sample or specimen) is exposed in the other aperture (15). The addition of extraction reagents to the recess, for example via aperture (14), enables reagent to accumulate in the head of the swab, thereby releasing any Strep.A antigen that may be present. After allowing time for this extraction, the test strip (20) is inserted under the cover strip (16) so that it makes liquid-conductive contact with the head of the swab at the origin of the test strip. Liquid migrates from the swab to the test strip, thereby developing the test result in the test strip.

In a further development of this embodiment of the testing device, the extraction reagents, or other reagents required in other test formats, may be blister packed within the housing so that the insertion of the swab bursts the blister packaging to the reagents.

In addition, some tests for pathogens (e.g. Strep.B, some pathogenic *E. coli*) require a period of culture to increase the concentration of the organism before testing. In this format, liquid culture medium may be added (or issued pre-packed) to the housing prior to insertion of the swab or other sample collection device in order to allow "onboard" culturing.

For specimens that require a specified volume of reagent, e.g. for semi-quantitative or quantitative assays, a specifically designed sample collection device may be used instead of a swab as described above. It is anticipated that the same generic housing illustrated above would be used with such a semi-quantitative or quantitative sample collection device.

Figure 3:
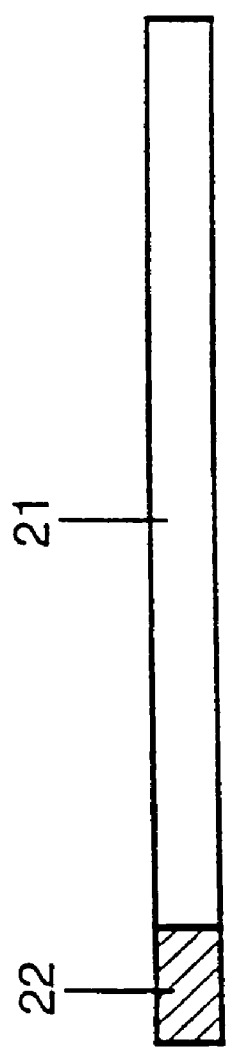
FIG. 3 illustrates an alternative sample collection device for use in the testing device of the present invention.

A preferred embodiment of such a collection device is illustrated in FIG. 3, and comprises a plastic handle (21), (e.g. of polystyrene or similar plastic) which has laminated thereto a hydrophilic matrix of defined absorptive volume (22). Suitable matrix materials include porous plastic, paper, non-woven synthetic fabrics, fibreglass, etc. Porous plastics made by Porex (Fairburn, Ga., USA) of high molecular weight polyethylene have been found to be particularly suitable. This collection device has the advantage that it may be manufactured inexpensively by established industrial web-handling, laminating and die-cutting processes.

In use, the matrix of the collection device is touched to the liquid to be sampled until it has absorbed its predetermined fill volume of sample. The collection device is then inserted into the recess in the housing and the test completed by insertion of the immunodiagnostic test strip as described above.

Persons skilled in the art will recognise that many modifications or variations may be made to the devices described in detail herein in order to suit other testing purposes or by way of adaptation for optimal function, without departing from the spirit and scope of the present invention as broadly described above.

The claims defining the invention are as follows:

1. A device for use in the collection and testing of a sample, comprising:
    a. a sample collection device;
    b. a housing having an internal recess open to the exterior via first and second apertures,
        wherein said first aperture and recess are adapted to receive at least a portion of said sample collection device inserted into said recess via said first aperture, and
    c. a cover strip sealing said second aperture and remaining open along one edge,
        wherein said cover strip is adapted to receive an insertable testing element inserted under said cover strip, and
        wherein said second aperture provides fluid communication between at least a portion of said sample collection device and said insertable testing element when inserted therein.

2. A testing device for use in the collection and testing of a sample, comprising:
    a. a sample collection device;
    b. a housing having a base and a cover, said base having a recess and said cover having first and second apertures connecting to said recess;
        wherein said recess and first aperture are adapted to receive at least a portion of said sample collection device inserted into said recess via said first aperture,
    c. a cover strip sealing said second aperture and remaining open along one edge,
        wherein said cover strip is adapted to receive an insertable testing element inserted under said cover strip, and
        wherein said second aperture provides fluid communication between said at least a portion of said sample collection device and said insertable testing element when inserted therein.

3. A device according to claim 1 or claim 2, wherein, on insertion of the testing element into the housing, the testing element is in direct liquid-conductive communication with a sample collected on the sample collection device.

4. A device according to claim 1 or claim 2, wherein the sample collection device is a swab.

5. A device according to claim 1 or claim 2, wherein the sample collection device collects a predetermined amount of the sample.

6. A device according to claim 5, wherein the sample collection device comprises a hydrophilic, porous matrix of defined volumetric capacity, affixed to the base of a dipstick or handle.

7. A device according to claim 1 or claim 2, wherein the housing further comprises a solvent application aperture in communication with the internal recess.

8. A device according to claim 1 or 2 wherein the housing is configured to position the test element so that a sample-carrying portion of the sample collection device is interposed between the housing and the testing element.

9. A device according to claim 1 or claim 2, wherein said device further comprises an insertable testing element.

10. A device according to claim 9, wherein the testing element is a guaiac-based test strip.

11. A device according to claim 9, which comprises two or more testing elements each of which, when inserted into the housing, is in liquid-conductive communication with a sample collected on the sample collection device.

12. A device according to claim 11, wherein the testing elements are the same elements.

13. A device according to claim 11, wherein the testing elements are different elements.

14. A device according to claim 11, wherein at least one of said testing elements is an immunochromatographic test strip.

15. A device according to claim 11, wherein at least one of said testing elements is a guaiac-based test strip.

16. A device according to claim 1 or claim 2, wherein said device further comprises a cover over said second aperture, wherein said cover is open on at least one side and adapted to receive said testing element.

17. A method for the identification of an analyte of interest in a sample, comprising:
   a. collecting a sample on a sample collection device,
   b. inserting at least a sample-carrying portion of said sample collection device into a housing having a base and a cover, said base having a recess and said cover having first and second apertures connecting to said recess;
      wherein said recess and first aperture are adapted to receive at least a portion of a sample collection device inserted into said recess via said first aperture,
      wherein said second aperture is sealed by a cover strip with the cover strip remaining open along one edge and said cover strip adapted to receive a testing element inserted under said cover strip, and
      wherein said second aperture provides fluid communication between said at least a portion of a sample collection device and said testing element when inserted therein, and
   c. subsequently inserting an insertable testing element under said cover strip such that the testing element is in liquid-conductive communication with said sample.

18. A method according to claim 17, further comprising:
   d. applying a solvent to said sample to enable transfer of at least part of said sample, or a component thereof, to the testing element.

19. A method according to claim 17 wherein the collecting step includes using the sample collection device to obtain the sample from a patient.

20. A method according to claim 19 wherein the sample collection device comprises a swab.

21. A method according to claim 19 wherein the sample collection device comprises a hydrophilic, porous matrix of defined volumetric capacity, affixed to the base of a dipstick or handle and configured to obtain a sample from the patient.

22. A method according to claim 17 wherein steps (b) and (c) are performed at different geographic locations.

23. A method according to claim 17 wherein steps (b) and (c) are performed on different dates.

24. A method according to claim 17 further comprising, between steps (b) and (c), allowing the sample to become dehydrated within the housing.

* * * * *